(12) United States Patent
Chang et al.

(10) Patent No.: US 10,005,997 B2
(45) Date of Patent: Jun. 26, 2018

(54) MULTI-FUNCTIONAL PORT FOR MICROALGAE CULTIVATION AND HARVESTING

(71) Applicant: KOREA DISTRICT HEATING CORP., Seongnam-si, Gyeonggi-do (KR)

(72) Inventors: Won Seok Chang, Goyang-si (KR); Deog Yong Ahn, Suwon-si (KR); Sang Ho Shin, Incheon (KR); Ji Hye Yu, Incheon (KR); Young Jae Lee, Daejeon (KR); Won Kwon Lee, Seoul (KR); Kwang Keun Choi, Seoul (KR); Sung Min Kim, Suwon-si (KR)

(73) Assignee: KOREA DISTRICT HEATING CORP., Seongnam-si, Gyeonggi-do (KR)

( * ) Notice: Subject to any disclaimer, the term of this patent is extended or adjusted under 35 U.S.C. 154(b) by 13 days.

(21) Appl. No.: 15/113,378

(22) PCT Filed: Jun. 1, 2016

(86) PCT No.: PCT/KR2016/005787
§ 371 (c)(1),
(2) Date: Jul. 21, 2016

(87) PCT Pub. No.: WO2017/111221
PCT Pub. Date: Jun. 29, 2017

(65) Prior Publication Data
US 2017/0204356 A1    Jul. 20, 2017

(30) Foreign Application Priority Data
Dec. 23, 2015 (KR) .................. 10-2015-0184946

(51) Int. Cl.
C12M 1/04 (2006.01)
C12M 1/26 (2006.01)
C12M 1/00 (2006.01)

(52) U.S. Cl.
CPC ............ *C12M 23/40* (2013.01); *C12M 33/00* (2013.01); *C12M 43/00* (2013.01)

(58) Field of Classification Search
CPC .................................................. C12M 23/40
USPC ......................................................... 422/539
See application file for complete search history.

(56) References Cited

U.S. PATENT DOCUMENTS

| 2010/0093073 A1* | 4/2010 | Erhardt et al. ......... C12M 29/26 435/289.1 |
| 2010/0236340 A1* | 9/2010 | Lee et al. ............... C12M 37/02 73/863.02 |

* cited by examiner

*Primary Examiner* — Kevin Joyner
*Assistant Examiner* — Holly M Mull
(74) *Attorney, Agent, or Firm* — Novick, Kim & Lee, PLLC; Jae Youn Kim

(57) ABSTRACT

The present invention relates to a port installed in a closed-ended photochemical reactor, and more particularly, to a multi-functional port for microalgae cultivation and harvesting that supplies gas for cultivation for culturing microalgae by connecting to the closed-ended photochemical reactor; supplies gas for prevention of precipitation for lifting microalgae during cultivation; and assembles by taking samples of microalgae or selectively combining a plurality of valves which can harvest microalgae, whose cultivation is completed.

2 Claims, 6 Drawing Sheets

MULTI-FUNCTIONAL PORT FOR MICROALGAE CULTIVATION AND HARVESTING

TECHNICAL FIELD

The present invention relates to a port installed in a closed-ended photochemical reactor, and more particularly, to a multi-functional port for microalgae cultivation and harvesting that supplies gas for cultivation for culturing microalgae by connecting to the closed-ended photochemical reactor; supplies gas for prevention of precipitation for lifting microalgae during cultivation; and assembles by taking samples of microalgae or selectively combining a plurality of valves which can harvest microalgae, whose cultivation is completed.

BACKGROUND ART

Due to emission of greenhouse gas caused by the use of fossil fuels, global warming has resulted in changes in climate and global environment, thereby threatening the survival of all living things on earth including human beings. Accordingly, various researches and developments for reducing carbon dioxide are now in progress. As one of efforts, study on the way of capturing and biologically converting carbon dioxide is actively underway.

As a green plant which performs photosynthesis for biologically converting carbon dioxide, microalgae have been actively studied. In common with other green plants in photosynthetic process, microalgae, phytoplankton, use sun as an energy source and grow up with photosynthesis for biofixation of carbon dioxide.

The first reason for recognizing microalgae as a means of biofixation of carbon dioxide is very low amount of energy to be injected for capturing carbon dioxide, because solar energy may be the main energy source as the same with absorption of carbon dioxide. Thus, since there is less amount of generating carbon dioxide for operation of biofixation of carbon dioxide, removal efficiency is high in terms of profit balance of carbon dioxide.

Secondly, required size of site is small because of very high speed of fixation of carbon dioxide as compared to green plants. According to results from study conducted at Tokyo Electric Power Research Institute, it is revealed that the speed of fixation of carbon dioxide of microalgae is more than 8 times higher than that of macroalgae and more than 16 times higher than that of pine trees, the most common tree in Korea.

Besides, there is an advantage in that processes for separating and concentrating carbon dioxide are not required due to direct fixation of carbon dioxide from combustion gas. Moreover, microalgae, generated from carbon dioxide fixation, contain numerous useful materials, thereby being utilized for manufacture of expensive bioproducts.

These microalgae are cultured by using open or closed-ended photochemical reactors. Especially, as for closed-ended photochemical reactors, there is a gradual increase in frequency of use because closed-ended photochemical reactors can culture more highly concentrated microalgae than those by open photochemical reactors and high value materials can be produced from the cultured microalgae. As for microalgae cultivation using such closed-ended photochemical reactors, a plurality of photochemical reactors having a few drops of culture fluid in terms of easy-to-use sunlight has to be used. To do so, gas with a constant amount (especially, carbon dioxide) has to be stably supplied to such multiple photochemical reactors.

However, there has been problems that it is mostly difficult to take samples due to characteristics of closed-ended photochemical reactors; agitation and light use efficiencies are reduced because microalgae is precipitated while cultivation is underway; and it is hard to harvest microalgae from a plurality of photochemical reactors after completion of cultivation.

PRIOR ART

Reference (Patent reference 1) Korean Patent Registration No. 10-1408239

(Patent reference 2) Korean Patent Publication No. 10-2012-0095826

DETAILED EXPLANATIONS OF THE INVENTION

Technical Problem

For solving above problems, the object of the present invention is to provide a multi-functional port for microalgae cultivation and harvesting that supplies gas for cultivation for culturing microalgae by connecting to a closed-ended photochemical reactor; supplies gas for prevention of precipitation for lifting microalgae during cultivation; and assembles by taking samples of microalgae or selectively combining a plurality of valves which can harvest microalgae, whose cultivation is completed.

Further, the other object of the present invention is to provide the multi-functional port for microalgae cultivation and harvesting that reduces waste of time and manpower in culturing microalgae, taking samples and harvesting by connecting the multi-functional ports for microalgae cultivation and harvesting each other and arranging multiple closed-ended photochemical reactors in a row.

Technical Solution

To accomplish above objects, the present invention is characterized by a multi-functional port for microalgae cultivation and harvesting comprising: a first one touch valve, T-shaped, for supplying each of gas for cultivation for culturing microalgae, which come from a gas supply tube line for cultivation, and gas for prevention of precipitation for lifting microalgae, which come from a gas supply tube line for prevention of precipitation, to the inside of a closed-ended photochemical reactor by inserting a gas supply tube for cultivation and a gas supply tube for prevention of precipitation to the inside of the closed-ended photochemical reactor, and for taking samples of microalgae cultured in the closed-ended photochemical reactor or discharging all microalgae to sampling and harvesting tube lines through the gas supply tube for prevention of precipitation; a second one touch valve, T-shaped, in which one end is connected to the first one touch valve with a connection tube; the other end is connected to the gas supply tube line for prevention of precipitation, thereby intermittently supplying the gas for prevention of precipitation to the first one touch valve; and microalgae is released from the first one touch valve to the other end, thereby being discharged to the sampling and harvesting tube lines; and a one touch hand valve for harvesting, I-shaped, in which one end is connected to the first one touch valve or the second one touch valve with the connection tube; and the other end is connected to the gas supply tube line for prevention of precipitation or the sampling and harvesting tube lines, thereby supplying the gas for prevention of precipitation to the first one touch valve or the second one touch valve or discharging microalgae, released from the first one touch valve or the second one touch valve, to the sampling and harvesting tube lines, wherein the port is combined to the closed-ended photochemical reactor which cultures microalgae.

Here, one end of the first one touch valve is connected to the gas supply tube for prevention of precipitation, and the other end penetrates the gas supply tube for prevention of precipitation, thereby being inserted into the inside of the closed-ended photochemical reactor.

Here, the end of the gas supply tube for cultivation comprises a gas disperser to disperse gas from the inside of the closed-ended photochemical reactor.

Here, one end of the first one touch valve is connected to an end tube for fixing the gas supply tube for cultivation; an I-shaped third one touch valve is penetrated and fixed to the end tube; one end of the third one touch valve is combined to the gas supply tube for cultivation; and the other end of the third one touch valve is connected to the gas supply tube line for cultivation.

Here, the gas supply tube line for cultivation is connected to the gas supply tube line for prevention of precipitation with a bypass tube line.

Here, the multi-functional port for microalgae cultivation and harvesting is mutually assembled to one closed-ended photochemical reactor or to each of the plurality of closed-ended photochemical reactors.

Here, in the multi-functional port for microalgae cultivation and harvesting, as for combination of the first one touch valve and the one touch hand valve for harvesting, the gas supply tube line for prevention of precipitation and the sampling and harvesting tube lines are used as a common tube line.

Advantageous Effects

According to a multi-functional port for microalgae cultivation and harvesting of the present invention, as constituted above, the essential constitutional element of closed-ended cultivation of microalgae is supply of gas with a constant amount to a closed-ended photochemical reactor, being used, by a steady flow, enabling to equally culture microalgae, which have been cultured in all closed-ended photochemical reactors being used, by preparing multi-functional ports to all closed-ended photochemical reactors.

Further, since the present invention enables to solve problems caused by precipitated cells and difficulties in taking samples and harvesting according to cultivation of microalgae, it enables to culture highly concentrated microalgae by effectively processing cultivation of microalgae using closed-ended photochemical reactors.

DESCRIPTION OF THE PREFERRED EMBODIMENTS

The configuration of a multi-functional port for microalgae cultivation and harvesting, according to the present invention, will be described in detail with the accompanying drawing.

In the following description of the present invention, a detailed description of known incorporated functions and configurations will be omitted when to include them would make the subject matter of the present invention rather unclear. Also, the terms used in the following description are defined taking into consideration the functions provided in the present invention. The definitions of these terms should be determined based on the whole content of this specification, because they may be changed in accordance with the option of a user or operator or a usual practice.

Figure 1:
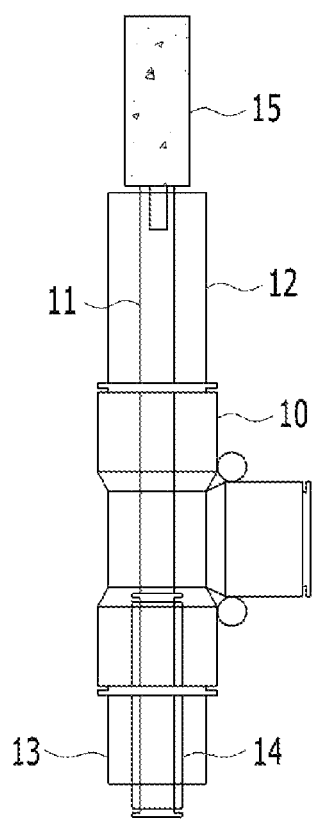
FIG. 1 is a sectional diagram showing the constitution of a first one touch valve of a multi-functional port for microalgae cultivation and harvesting according to the present invention.
Figure 2:
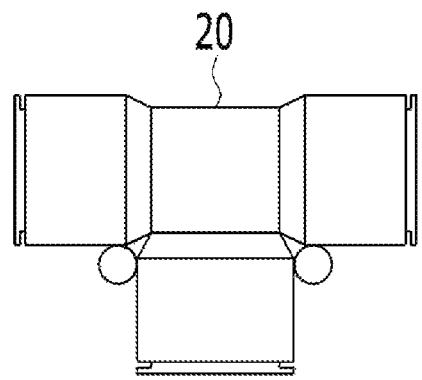
FIG. 2 is a sectional diagram showing the constitution of a second one touch valve of the multi-functional port for microalgae cultivation and harvesting according to the present invention.
Figure 3:
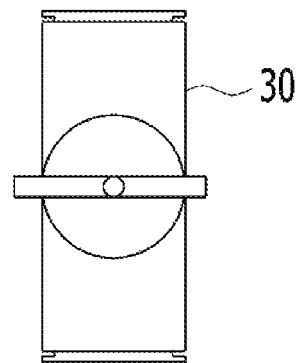
FIG. 3 is a sectional diagram showing the constitution of a one touch hand valve for harvesting of the multi-functional port for microalgae cultivation and harvesting according to the present invention.
Figure 4:
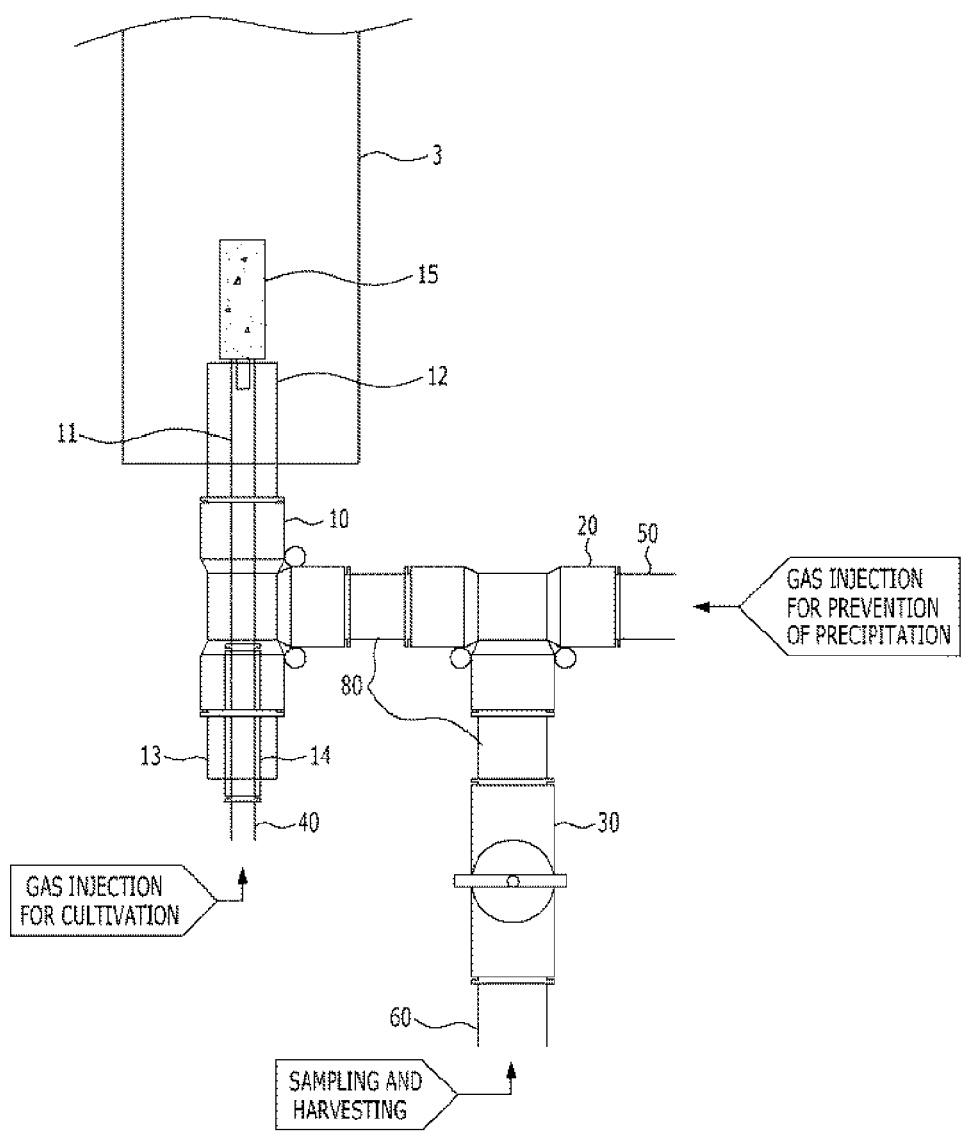
FIGS. 4 and 5 are states of use showing that the multi-functional port for microalgae cultivation and harvesting according to the present invention is installed to a closed-ended reactor.
Figure 5:
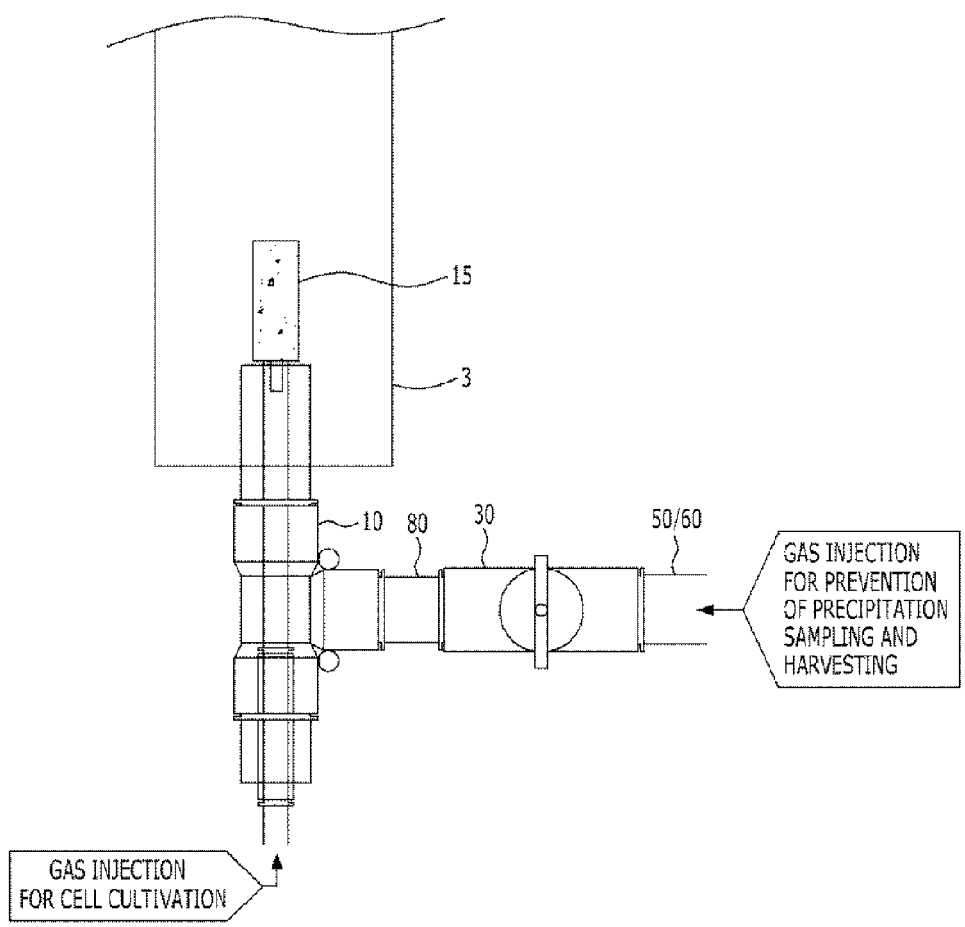
Figure 6:
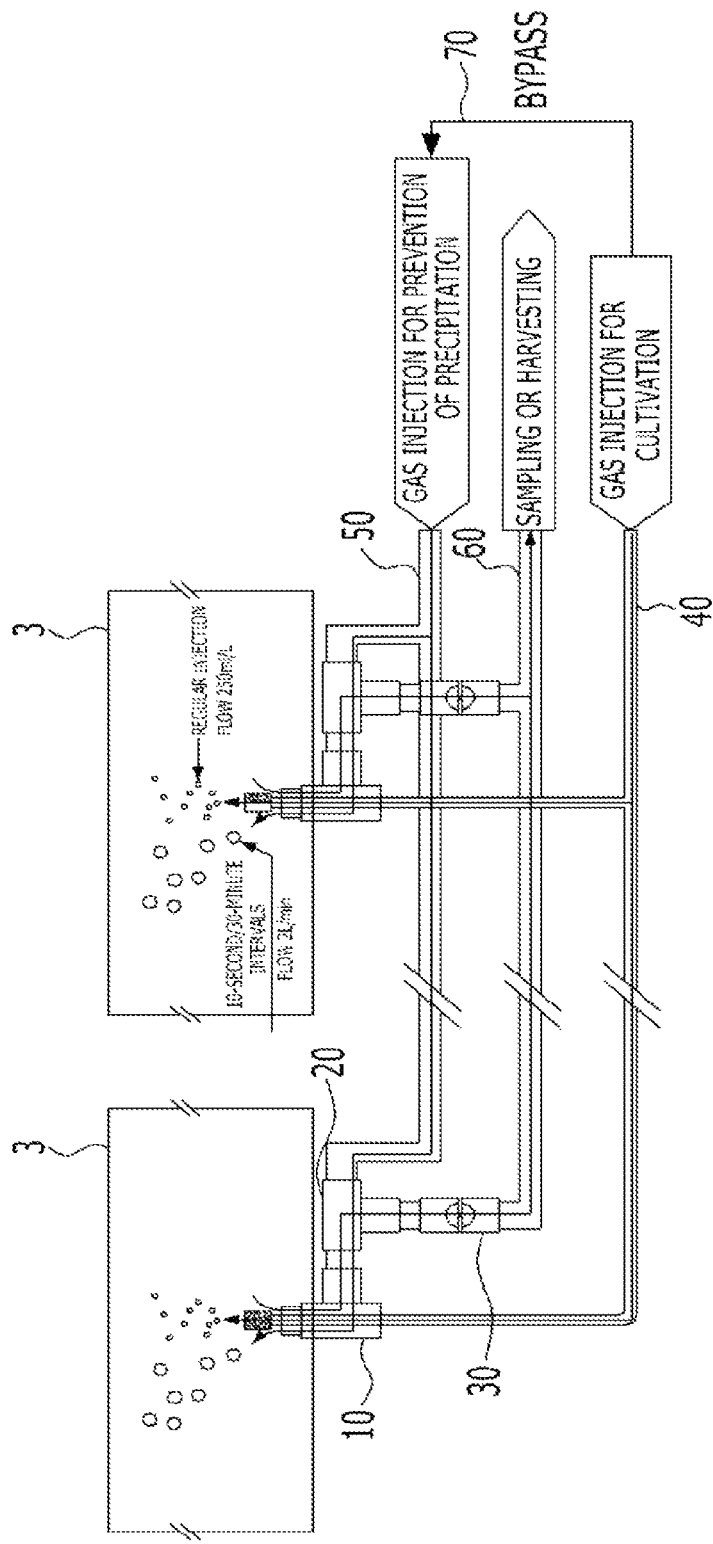
FIGS. 6 and 7 are states of use showing that the multi-functional port for microalgae cultivation and harvesting according to the present invention is installed to a plurality of closed-ended photochemical reactors.
Figure 7:
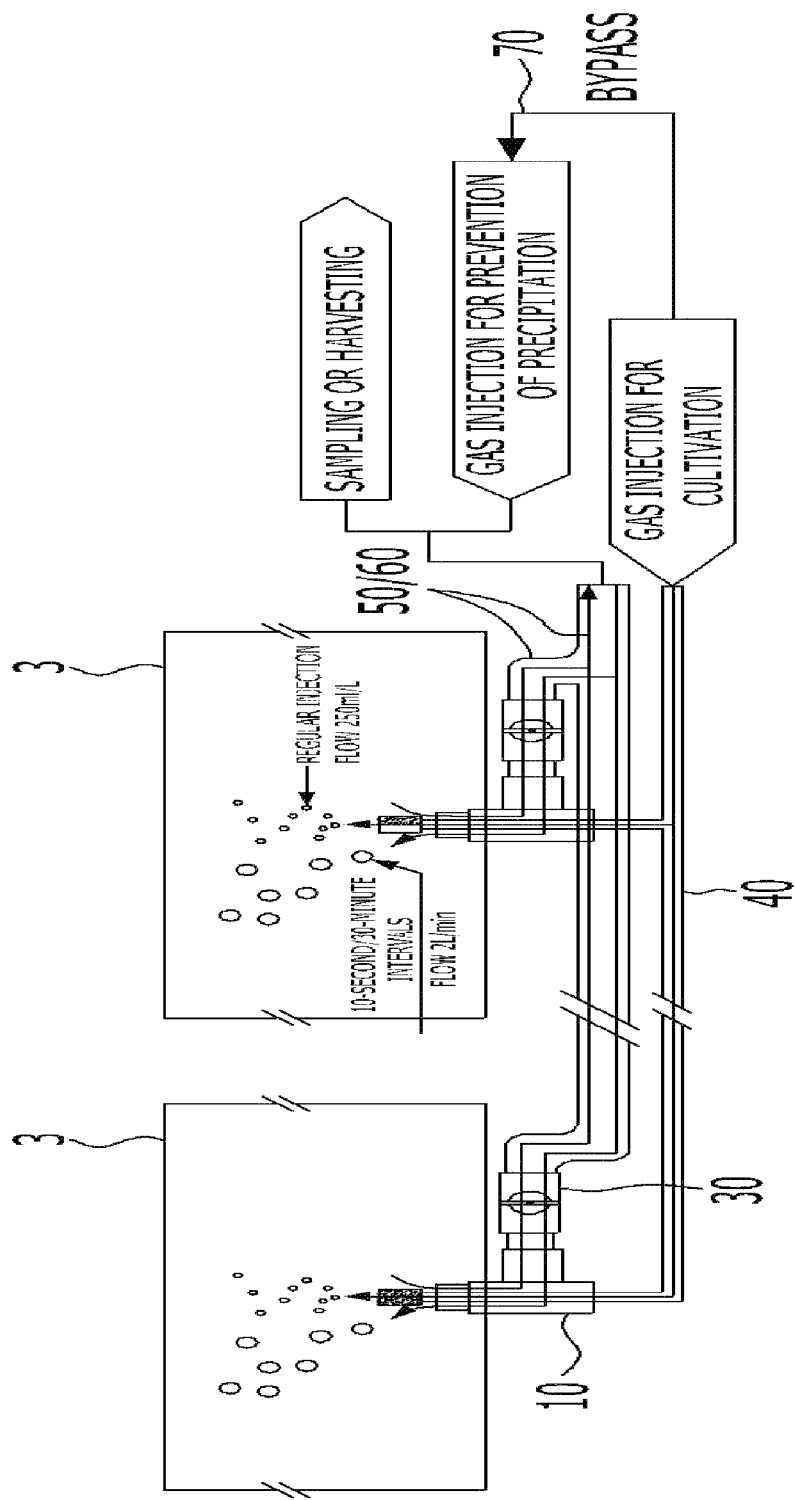

FIG. 1 is a sectional diagram showing the constitution of a first one touch valve of a multi-functional port for microalgae cultivation and harvesting according to the present invention. FIG. 2 is a sectional diagram showing the constitution of a second one touch valve of the multi-functional port for microalgae cultivation and harvesting according to the present invention. FIG. 3 is a sectional diagram showing the constitution of a one touch hand valve for harvesting of the multi-functional port for microalgae cultivation and harvesting according to the present invention. FIGS. 4 and 5 are states of use showing that the multi-functional port for microalgae cultivation and harvesting according to the present invention is installed to a closed-ended reactor. FIGS. 6 and 7 are states of use showing that the multi-functional port for microalgae cultivation and harvesting according to the present invention is installed to a plurality of closed-ended photochemical reactors.

Referring to FIGS. 1 to 7, a multi-functional port for microalgae cultivation and harvesting (1) according to the present invention consists of a first one touch valve (10), a second one touch valve (20), and a one touch hand valve for harvesting (30).

Further, the first one touch valve (10) consists of a common T-shaped one touch valve (or one touch fitting), for supplying each of gas for cultivation for culturing microalgae, which come from a gas supply tube line for cultivation (40), and gas for prevention of precipitation for lifting microalgae, which come from a gas supply tube line for prevention of precipitation (50), to the inside of a closed-ended photochemical reactor by inserting a gas supply tube for cultivation (11) and a gas supply tube for prevention of precipitation (12) to the inside of the closed-ended photochemical reactor (3), and for taking samples of microalgae cultured in the closed-ended photochemical reactor (3) or discharging all microalgae to sampling and harvesting tube lines (60) through the gas supply tube for prevention of precipitation (12). Here, one end of the first one touch valve

(10) is connected to an end tube (13) for fixing the gas supply tube for cultivation (11); an I-shaped third one touch valve (14) is penetrated and fixed to the end tube (13); one end of the third one touch valve (14) is combined to the gas supply tube for cultivation (11); and the other end of the third one touch valve (14) is connected to the gas supply tube line for cultivation (40). Here, it is desirable that the end of the gas supply tube for cultivation (11) comprises a gas disperser (15) to disperse gas from the inside of the closed-ended photochemical reactor (3); the closed-ended photochemical reactor (3) is applied to an agitated reactor, a disc reactor, a column reactor, a high molecular film reactor, etc.; and the gas supply tube line for cultivation (40) is connected to the gas supply tube line for prevention of precipitation (50) with a bypass tube line (70).

Further, the second one touch valve (20) consists of a common T-shaped one touch valve (or one touch fitting) in which one end is connected to the first one touch valve (10) with a connection tube (80); the other end is connected to the gas supply tube line for prevention of precipitation (50), thereby intermittently supplying the gas for prevention of precipitation to the first one touch valve (10); and microalgae is released from the first one touch valve (10) to the other end, thereby being discharged to the sampling and harvesting tube lines (60).

Furthermore, the one touch hand valve for harvesting (30) consists of a common I-shaped one touch valve in which one end is connected to the first one touch valve (10) or the second one touch valve (20) with the connection tube (80); and the other end is connected to the gas supply tube line for prevention of precipitation (50) or the sampling and harvesting tube lines (60), thereby supplying the gas for prevention of precipitation to the first one touch valve (10) or the second one touch valve (20) or discharging microalgae, released from the first one touch valve (10) or the second one touch valve (20), to the sampling and harvesting tube lines (60).

Meanwhile, in the multi-functional port for microalgae cultivation and harvesting (1) according to the present invention, one closed-ended photochemical reactor (3) may be installed by all connecting to the first one touch valve (10), the second one touch valve (20), and the one touch hand valve for harvesting (30) as illustrated in FIG. 4, or the first one touch valve (10) may be installed by combining the one touch hand valve for harvesting (30) as illustrated in FIG. 5.

Also, in the multi-functional port for microalgae cultivation and harvesting (1) according to the present invention, a plurality of closed-ended photochemical reactors (3) may be installed by all connecting to the first one touch valve (10), the second one touch valve (20), and the one touch hand valve for harvesting (30) as illustrated in FIG. 5, or the first one touch valve (10) may be installed by combining the one touch hand valve for harvesting (30) as illustrated in FIG. 7. At this time, as for combination of the first one touch valve (10) and the one touch hand valve for harvesting (30), the gas supply tube line for prevention of precipitation (50) and the sampling and harvesting tube lines (60) are used as a common tube line as illustrated in FIG. 7.

Hereinafter, operations of the multi-functional port for microalgae cultivation and harvesting according to the present invention will be described in detail with the accompanying drawings.

First, as illustrated in FIGS. 4 and 5, there may be two types of the multi-functional ports for microalgae cultivation and harvesting (1) according to the present invention, and their forms may be different depending on characteristics of microalgae as well.

All combining the first one touch valve (10), the second one touch valve (20), and one touch hand valve for harvesting (30), FIG. 4 may be used in microalgae whose speed of precipitation is pretty fast. Only combining the first one touch valve (10) and the one touch hand valve for harvesting (30), FIG. 5 may be used in microalgae whose speed of precipitation is not fast or which is not precipitated at all.

Further, the gas supply tube for cultivation (11) and the gas supply tube for prevention of precipitation (12) of the first one touch valve (10) may be attached to a proper position at a bottom of a closed-ended photochemical photobioreactor (2). Here, it may be defined that the proper position refers to a location where density of gas is evenly supplied to the inside of the closed-ended photochemical photobioreactor (2), or a location where gas is supplied to evenly mix microalgae in accordance with gas supply. Thus, an attachment location such as a bottom center of the closed-ended photochemical photobioreactor (2) is not defined. Also, in case that there is an expectation to damage the closed-ended photochemical photobioreactor (2) due to weight of the multi-functional port for microalgae cultivation and harvesting (1), a supplementary fixation device may be added for installing and fixing the multi-functional port (1).

As for FIG. 4, during microalgae cultivation, gas for cultivation from the gas supply tube line for cultivation (40) is continuously supplied to the closed-ended photochemical photobioreactor (2) through the gas supply tube for cultivation (11); and in case that precipitation amount or speed of precipitation of microalgae is getting faster during microalgae cultivation, gas for prevention of precipitation of the gas supply tube line for prevention of precipitation (50) is periodically supplied once for 30 minutes through the second one touch valve (20) and the gas supply tube for prevention of precipitation (12), thereby lifting precipitated microalgae. Here, periods of supply may be different depending on a speed of precipitation of microalgae, being cultured.

Further, in case that taking samples is required for recognition of characteristics of microalgae or badges during microalgae cultivation, samples are taken through the gas supply tube for prevention of precipitation (12) of the one touch valve (10), the second one touch valve (20), one touch hand valve for harvesting (30) and sampling and harvesting tube lines (60) by opening the one touch hand valve for harvesting (30). At this time, it is desirable that gas from the gas supply tube for cultivation (11) is blocked for uniform sampling in consideration of characteristics of cultivation of microorganisms, and samples are taken by the one touch hand valve for harvesting (30).

As for FIG. 5, gas is continuously supplied by the gas supply tube for cultivation (11) during microalgae cultivation; and in case that taking samples are required or harvesting is required after completion of cultivation, samples are taken through the gas supply tube for prevention of precipitation (12) of the one touch valve (10), one touch hand valve for harvesting (30) and sampling and harvesting tube lines (60) by opening the one touch hand valve for harvesting (30). At this time, it is desirable that gas from the gas supply tube for cultivation (11) is blocked for uniform sampling in consideration of characteristics of cultivation of microorganisms, and samples are taken by the one touch hand valve for harvesting (30).

Furthermore, gas for prevention of precipitation of the gas supply tube line for prevention of precipitation (50) is periodically supplied once for 30 minutes through the one touch hand valve for harvesting (30) and the gas supply tube for prevention of precipitation (12), thereby lifting precipitated microalgae.

FIGS. 6 and 7 show connection status of two types of the multi-functional port for microalgae cultivation and harvesting provided by the present invention.

As illustrated in FIGS. 6 and 7, all closed-ended photochemical reactors (3) may be arranged in a row and operated by using the multi-functional port (1). At this time, in case that there is an expectation to damage the closed-ended photochemical photobioreactor (2) due to weight of the multi-functional port for microalgae cultivation and harvesting (1), a supplementary fixation device may be added for installing and fixing the multi-functional port (1). Also, gas is regularly supplied at a flow (250 ml/min) through a gas injection device (not illustrated) connected to the gas supply tube line for cultivation (40); and gas is supplied at a flow (2 l/min) for 10 seconds every half hour through a gas injection device (not illustrated) connected to the gas supply tube line for prevention of precipitation (50). At this time, if there are precipitated cells, there will be lifted and dispersed by a momentary aeration, and gas injection for prevention of precipitation will be used as pre-work for sampling.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

EXPLANATION OF REFERENCE NUMBERS

1: multi-functional port
3: closed-ended photochemical reactor
10: first one touch valve
11: gas supply tube for cultivation
12: gas supply tube for prevention of precipitation
13: end tube
14: third one touch valve
20: second one touch valve
30: one touch hand valve for harvesting
40: gas supply tube line for cultivation
50: gas supply tube line for prevention of precipitation
60: sampling and harvesting tube lines
70: bypass tube line
80: connection tube

The invention claimed is:

1. A multi-functional port for microalgae cultivation and harvesting comprising:
    a first one touch valve, T-shaped, connecting a first gas supply tube line for the cultivation with a first gas supply tube, connecting a first connection tube for prevention of precipitation with a second gas supply tube, wherein the first gas supply tube for the cultivation and the second gas supply tube for the prevention of precipitation are coupled to a close-ended photochemical reactor and an end of the first gas supply tube and an end of the second gas supply tube are located inside the close-ended photochemical reactor, for supplying gas for the cultivation for culturing microalgae, which comes from the first gas supply tube line for the cultivation, and gas for the prevention of precipitation for lifting the microalgae, which comes from the first connection tube for the prevention of precipitation, to an inside of the close-ended photochemical reactor, and for taking samples of microalgae cultured in the close-ended photochemical reactor or discharging the cultured microalgae from the close-ended photochemical reactor to a sampling and harvesting tube line through the second gas supply tube for the prevention of precipitation;
    a second one touch valve, T-shaped, in which a first end of the second one touch valve is connected to the first one touch valve through the first connection tube; a second end of the second one touch valve is connected to a gas supply tube line for the prevention of precipitation, thereby intermittently supplying the gas for the prevention of precipitation to the first one touch valve; and the cultured microalgae is released from the first one touch valve to a third end of the second one touch valve, thereby being discharged to the sampling and harvesting tube line; and
    a one touch hand valve for harvesting, I-shaped, in which one end is connected to the second one touch valve with a second connection tube; and the other end is connected to the sampling and harvesting tube line, thereby discharging the cultured microalgae, released from the third end of the second one touch valve, to the sampling and harvesting tube line,
    wherein the port is combined to the close-ended photochemical reactor which cultures microalgae,
    wherein the first gas supply tube for the cultivation penetrates the second gas supply tube for the prevention of precipitation and is inserted into the inside of the close-ended photochemical reactor,
    wherein one end of the first gas supply tube for the cultivation comprises a gas disperser to disperse gas from the inside of the close-ended photochemical reactor,
    wherein one end of the first one touch valve is connected to an end tube for fixing the first gas supply tube for the cultivation; an I-shaped third one touch valve penetrates and is fixed to the end tube; one end of the I-shaped third one touch valve is combined to the first gas supply tube for the cultivation; and the other end of the I-shaped third one touch valve is connected to the first gas supply tube line for the cultivation, and
    wherein the first gas supply tube line for the cultivation is connected to the second gas supply tube line for the prevention of precipitation with a bypass tube line.

2. A multi-functional port for microalgae cultivation and harvesting, comprising:
    a first one touch valve, T-shaped, connecting a first gas supply tube line for the cultivation with a first gas supply tube, connecting a connection tube for prevention of precipitation with a second gas supply tube, wherein the first gas supply tube for the cultivation and the second gas supply tube for the prevention of precipitation are coupled to a close-ended photochemical reactor and an end of the first gas supply tube and an end of the second gas supply tube are located inside the close-ended photochemical reactor, for supplying gas for culturing microalgae, which comes from the first gas supply tube line for the cultivation, and gas for the prevention of precipitation for lifting the microalgae, which comes from the connection tube for the prevention of precipitation, to an inside of the close-ended photochemical reactor, and for taking samples of microalgae cultured in the close-ended photochemical reactor or discharging the cultured microalgae from the close-ended photochemical reactor to a sampling and harvesting tube line through the second gas supply tube for the prevention of precipitation;

a one touch hand valve for harvesting, I-shaped, in which one end of the one touch hand valve is connected to the first one touch valve through the connection tube; and the other end of the one touch hand valve is connected to the second gas supply tube line for the prevention of precipitation and the sampling and harvesting tube line, thereby supplying the gas for the prevention of precipitation to the first one touch valve and discharging the cultured microalgae released from the first one touch valve to the sampling and harvesting tube line, wherein the port is combined to the close-ended photochemical reactor which cultures microalgae, wherein the first gas supply tube for the cultivation penetrates the second gas supply tube for the prevention of precipitation and is inserted into the inside of the close-ended photochemical reactor, wherein one end of the first gas supply tube for the cultivation comprises a gas disperser to disperse gas from the inside of the close-ended photochemical reactor, wherein one end of the first one touch valve is connected to an end tube for fixing the first gas supply tube for the cultivation; an I-shaped third one touch valve penetrates and is fixed to the end tube; one end of the I-shaped third one touch valve is combined to the first gas supply tube for the cultivation; and the other end of the I-shaped third one touch valve is connected to the first gas supply tube line for the cultivation, and wherein the first gas supply tube line for the cultivation is connected to the second gas supply tube line for the prevention of precipitation with a bypass tube line, and wherein the second gas supply tube line for the prevention of precipitation and the sampling and harvesting tube line constitute one common tube line.

\* \* \* \* \*